US012127882B2

(12) United States Patent
Hutchins et al.

(10) Patent No.: US 12,127,882 B2
(45) Date of Patent: Oct. 29, 2024

(54) MULTIMODAL IMAGING SYSTEMS PROBES AND METHODS

(71) Applicant: LightLab Imaging, Inc., Westford, MA (US)

(72) Inventors: Christopher Hutchins, Londonderry, NH (US); Michael Atlas, Arlington, MA (US); Terence Barnes, Lowell, MA (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 17/878,564

(22) Filed: Aug. 1, 2022

(65) Prior Publication Data

US 2022/0361847 A1 Nov. 17, 2022

Related U.S. Application Data

(63) Continuation of application No. 13/758,528, filed on Feb. 4, 2013, now Pat. No. 11,701,089.
(Continued)

(51) Int. Cl.
*A61B 8/00* (2006.01)
*A61B 5/00* (2006.01)
*A61B 8/12* (2006.01)

(52) U.S. Cl.
CPC .......... *A61B 8/4416* (2013.01); *A61B 5/0035* (2013.01); *A61B 5/0066* (2013.01);
(Continued)

(58) Field of Classification Search
CPC ....... A61B 8/4416; A61B 8/12; A61B 5/6852; A61B 5/0084; A61B 5/0066;
(Continued)

(56) References Cited

U.S. PATENT DOCUMENTS 5,039,193 A 8/1991 Snow et al.
5,076,279 A 12/1991 Arenson et al.
(Continued)

FOREIGN PATENT DOCUMENTS

EP 2484288 A1 8/2012
JP S61103436 A 5/1986
(Continued)

OTHER PUBLICATIONS

Yin et al. 2011 J.Biomed. Optics 16:060505-1-060505-3 (Year: 2011).*

(Continued)

*Primary Examiner* — Keith M Raymond
*Assistant Examiner* — Patrick M Mehl
(74) *Attorney, Agent, or Firm* — Lerner David LLP

(57) ABSTRACT

In part, the invention relates to a probe suitable for use with image data collection system. The probe, in one embodiment, includes an optical transceiver, such as a beam director, and an acoustic transceiver such as an ultrasound transducer. The optical transceiver is in optical communication with an optical fiber in optical communication with a beam director configured to transmit light and receive scattered light from a sample such as a wall of a blood vessel. The acoustic transceiver includes an ultrasound device or subsystem such as a piezoelectric element configured to generate acoustic waves and receive reflected acoustic waves from the sample.

19 Claims, 10 Drawing Sheets

Related U.S. Application Data

(60) Provisional application No. 61/727,997, filed on Nov. 19, 2012, provisional application No. 61/728,006, filed on Nov. 19, 2012.

(52) U.S. Cl.
CPC .......... *A61B 5/0084* (2013.01); *A61B 5/6852* (2013.01); *A61B 8/12* (2013.01); *A61B 2562/0204* (2013.01); *A61B 2562/0233* (2013.01)

(58) Field of Classification Search
CPC .......... A61B 5/0035; A61B 2562/0233; A61B 2562/0204; A61B 8/00; A61B 8/455; A61B 5/0095; A61B 5/05
See application file for complete search history.

(56) References Cited

U.S. PATENT DOCUMENTS

| | | | |
|---|---|---|---|
| 5,274,551 A | 12/1993 | Corby, Jr. | |
| 5,293,873 A | 3/1994 | Fang | |
| 5,313,949 A | 5/1994 | Yock | |
| 5,321,501 A | 6/1994 | Swanson et al. | |
| 5,335,662 A | 8/1994 | Kimura et al. | |
| 5,350,377 A | 9/1994 | Winston et al. | |
| 5,459,570 A | 10/1995 | Swanson et al. | |
| 5,465,147 A | 11/1995 | Swanson | |
| 5,503,155 A | 4/1996 | Salmon et al. | |
| 5,509,093 A | 4/1996 | Miller et al. | |
| 5,582,178 A | 12/1996 | Yock | |
| 5,588,434 A | 12/1996 | Fujimoto | |
| 5,619,368 A | 4/1997 | Swanson | |
| 5,748,598 A | 5/1998 | Swanson et al. | |
| 5,784,352 A | 7/1998 | Swanson et al. | |
| 5,830,145 A | 11/1998 | Tenhoff | |
| 5,965,355 A | 10/1999 | Swanson et al. | |
| 6,036,648 A | 3/2000 | White et al. | |
| 6,111,645 A | 8/2000 | Tearney et al. | |
| 6,129,667 A | 10/2000 | Dumoulin et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,217,527 B1 | 4/2001 | Selmon et al. | |
| 6,226,546 B1 | 5/2001 | Evans | |
| 6,265,792 B1 | 7/2001 | Granchukoff | |
| 6,282,011 B1 | 8/2001 | Tearney et al. | |
| 6,299,622 B1 | 10/2001 | Snow et al. | |
| 6,421,164 B2 | 7/2002 | Tearney et al. | |
| 6,423,002 B1 | 7/2002 | Hossack | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,585,660 B2 | 7/2003 | Dorando et al. | |
| 6,612,304 B1 | 9/2003 | Cise et al. | |
| 6,706,004 B2 | 3/2004 | Tearney et al. | |
| 6,847,454 B2 | 1/2005 | Crowley et al. | |
| 6,879,851 B2 | 4/2005 | McNamara et al. | |
| 6,891,984 B2 | 5/2005 | Petersen et al. | |
| 6,947,787 B2 | 9/2005 | Webler | |
| 7,134,994 B2 | 11/2006 | Alpert et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,366,562 B2 | 4/2008 | Dukesherer et al. | |
| 7,414,779 B2 | 8/2008 | Huber et al. | |
| 7,415,049 B2 | 8/2008 | Flanders et al. | |
| 7,477,763 B2 | 1/2009 | Willis et al. | |
| 7,605,681 B2 | 10/2009 | Wobben | |
| 7,621,874 B2 | 11/2009 | Romley et al. | |
| 7,625,366 B2 | 12/2009 | Atlas | |
| 7,729,745 B2 | 6/2010 | Maschke | |
| 7,751,865 B2 | 7/2010 | Jascob et al. | |
| 7,785,261 B2 | 8/2010 | Maschke | |
| 7,813,609 B2 | 10/2010 | Petersen et al. | |
| 7,818,044 B2 | 10/2010 | Dukesherer et al. | |
| 7,822,464 B2 | 10/2010 | Maschke et al. | |
| 7,840,253 B2 | 11/2010 | Tremblay et al. | |
| 7,848,791 B2 | 12/2010 | Schmitt et al. | |
| 7,916,387 B2 | 3/2011 | Schmitt | |
| 7,935,060 B2 | 5/2011 | Schmitt et al. | |
| 8,100,833 B2 | 1/2012 | Hirota | |
| 8,116,605 B2 | 2/2012 | Petersen et al. | |
| 8,162,834 B2 | 4/2012 | Feldman et al. | |
| 8,206,377 B2 | 6/2012 | Petroff | |
| 8,214,010 B2 | 7/2012 | Courtney et al. | |
| 8,325,419 B2 | 12/2012 | Schmitt | |
| 8,358,461 B2 | 1/2013 | Huber et al. | |
| 8,412,312 B2 | 4/2013 | Judell et al. | |
| 8,449,468 B2 | 5/2013 | Petersen et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,548,567 B2 | 10/2013 | Maschke et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,660,389 B2 | 2/2014 | Jono et al. | |
| 8,687,201 B2 | 4/2014 | Adler | |
| 8,786,336 B1 | 7/2014 | Schmitt | |
| 8,831,321 B1 | 9/2014 | Elbasiony | |
| 8,948,228 B2 | 2/2015 | Adler | |
| 8,953,911 B1 | 2/2015 | Xu et al. | |
| 2001/0031919 A1 | 10/2001 | Strommer et al. | |
| 2002/0019644 A1 | 2/2002 | Hastings et al. | |
| 2002/0049375 A1 | 4/2002 | Strommer et al. | |
| 2002/0161351 A1 | 10/2002 | Samson et al. | |
| 2003/0077043 A1 | 4/2003 | Hamm et al. | |
| 2003/0114869 A1 | 6/2003 | Nash et al. | |
| 2005/0025797 A1 | 2/2005 | Wang et al. | |
| 2005/0043618 A1 | 2/2005 | Mansouri-Ruiz | |
| 2005/0075574 A1 | 4/2005 | Furnish et al. | |
| 2005/0101859 A1 | 5/2005 | Maschke | |
| 2005/0113685 A1 | 5/2005 | Maschke et al. | |
| 2005/0149002 A1 | 7/2005 | Wang et al. | |
| 2005/0162237 A1 | 7/2005 | Yamashita | |
| 2005/0201662 A1 | 9/2005 | Petersen et al. | |
| 2005/0261582 A1 | 11/2005 | Becker et al. | |
| 2005/0279914 A1 | 12/2005 | Dimsdale et al. | |
| 2005/0288582 A1 | 12/2005 | Yu et al. | |
| 2006/0005861 A1 | 1/2006 | Lynn | |
| 2006/0025677 A1 | 2/2006 | Verard et al. | |
| 2006/0058614 A1 | 3/2006 | Tsujita | |
| 2006/0058622 A1 | 3/2006 | Tearney et al. | |
| 2006/0084867 A1 | 4/2006 | Tremblay et al. | |
| 2006/0093276 A1 | 5/2006 | Bouma et al. | |
| 2006/0095065 A1 | 5/2006 | Tanimura et al. | |
| 2006/0100489 A1 | 5/2006 | Pesach et al. | |
| 2006/0116577 A1 | 6/2006 | DeWitt | |
| 2006/0173299 A1 | 8/2006 | Romley et al. | |
| 2006/0241465 A1 | 10/2006 | Huennekens et al. | |
| 2006/0241572 A1 | 10/2006 | Zhou | |
| 2006/0247529 A1 | 11/2006 | Rose et al. | |
| 2007/0038061 A1 | 2/2007 | Huennekens et al. | |
| 2007/0060822 A1 | 3/2007 | Alpert et al. | |
| 2007/0100239 A1* | 5/2007 | Nair | G01S 7/52087 600/443 |
| 2007/0167833 A1* | 7/2007 | Redel | A61B 5/6852 600/476 |
| 2007/0232933 A1 | 10/2007 | Gille et al. | |
| 2007/0243137 A1 | 10/2007 | Hainfeld | |
| 2008/0114254 A1 | 5/2008 | Matcovitch et al. | |
| 2008/0123911 A1 | 5/2008 | Lam et al. | |
| 2008/0161696 A1 | 7/2008 | Schmitt et al. | |
| 2008/0171937 A1 | 7/2008 | Dukesherer et al. | |
| 2008/0177138 A1 | 7/2008 | Courtney et al. | |
| 2008/0177139 A1 | 7/2008 | Courtney et al. | |
| 2008/0177183 A1* | 7/2008 | Courtney | G02B 23/2423 600/463 |
| 2008/0180683 A1 | 7/2008 | Kemp | |

(56) References Cited

U.S. PATENT DOCUMENTS

| | | |
|---|---|---|
| 2008/0269572 A1 | 10/2008 | Kanz et al. |
| 2008/0287795 A1 | 11/2008 | Klingensmith et al. |
| 2009/0003031 A1 | 1/2009 | Kimura |
| 2009/0018393 A1 | 1/2009 | Dick et al. |
| 2009/0025398 A1 | 1/2009 | Muller et al. |
| 2009/0030312 A1 | 1/2009 | Hadjicostis |
| 2009/0043191 A1 | 2/2009 | Castella et al. |
| 2009/0174931 A1 | 7/2009 | Huber et al. |
| 2009/0195514 A1 | 8/2009 | Glynn et al. |
| 2009/0244545 A1 | 10/2009 | Toida |
| 2009/0253989 A1 | 10/2009 | Caplan et al. |
| 2009/0264768 A1 | 10/2009 | Courtney et al. |
| 2009/0270737 A1 | 10/2009 | Thornton |
| 2009/0299195 A1 | 12/2009 | Muller et al. |
| 2009/0306520 A1 | 12/2009 | Schmitt et al. |
| 2010/0076320 A1 | 3/2010 | Petersen et al. |
| 2010/0152590 A1 | 6/2010 | Moore et al. |
| 2010/0160788 A1 | 6/2010 | Davies et al. |
| 2010/0210939 A1 | 8/2010 | Hartmann et al. |
| 2010/0234736 A1 | 9/2010 | Corl |
| 2010/0249588 A1 | 9/2010 | Knight |
| 2010/0274124 A1 | 10/2010 | Jascob et al. |
| 2011/0025148 A1 | 2/2011 | Fukunaga et al. |
| 2011/0058178 A1 | 3/2011 | Tearney et al. |
| 2011/0071404 A1 | 3/2011 | Schmitt et al. |
| 2011/0098572 A1 | 4/2011 | Chen et al. |
| 2011/0101207 A1 | 5/2011 | Schmitt |
| 2011/0137399 A1* | 6/2011 | Chomas ............ A61M 25/0075 623/1.12 |
| 2011/0157686 A1 | 6/2011 | Huber et al. |
| 2011/0164255 A1 | 7/2011 | Konno et al. |
| 2011/0172511 A1* | 7/2011 | Schmitt ............. A61B 5/0066 600/407 |
| 2011/0178398 A1* | 7/2011 | Tearney ............. A61B 5/0084 600/431 |
| 2011/0178409 A1 | 7/2011 | Harris et al. |
| 2011/0190586 A1 | 8/2011 | Kemp |
| 2011/0228280 A1 | 9/2011 | Schmitt et al. |
| 2011/0251487 A1 | 10/2011 | Magnin et al. |
| 2012/0069348 A1 | 3/2012 | Jono et al. |
| 2012/0108979 A1 | 5/2012 | Franklin et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0253185 A1 | 10/2012 | Furuichi |
| 2012/0283564 A1 | 11/2012 | Ebbini et al. |
| 2012/0283569 A1 | 11/2012 | Ciompi et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff et al. |
| 2013/0072805 A1 | 3/2013 | Schmitt et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094697 A1 | 4/2014 | Petroff et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0119707 A1 | 4/2015 | Schmitt |
| 2015/0153157 A1 | 6/2015 | Schmitt et al. |
| 2015/0192405 A1 | 7/2015 | Schmitt |
| 2015/0297373 A1 | 10/2015 | Schmitt et al. |

FOREIGN PATENT DOCUMENTS

| | | | |
|---|---|---|---|
| JP | H05-329156 A | 12/1993 | |
| JP | H09168538 A | 6/1997 | |
| JP | H1156752 A | 3/1999 | |
| JP | H11276484 A | 10/1999 | |
| JP | 2002153472 A | 5/2002 | |
| JP | 2002528205 A | 9/2002 | |
| JP | 2004290548 A | 10/2004 | |
| JP | 2004357901 A | 12/2004 | |
| JP | 2005-095624 A | 4/2005 | |
| JP | 2005150198 A | 6/2005 | |
| JP | 2005-533533 A | 11/2005 | |
| JP | 2006280449 A | 10/2006 | |
| JP | 2008510586 A | 4/2008 | |
| JP | 2008521022 A | 6/2008 | |
| JP | 2008191022 A | 8/2008 | |
| JP | 2009101177 A | 5/2009 | |
| JP | 2009172118 A | 8/2009 | |
| JP | 2009183416 A | 8/2009 | |
| JP | 2009183417 A | 8/2009 | |
| JP | 2010508973 A | 3/2010 | |
| JP | 2010-516305 A * | 5/2010 | ............... A61B 8/12 |
| JP | 2010516304 A | 5/2010 | |
| JP | 2010-125273 A | 6/2010 | |
| JP | 2011072597 A | 4/2011 | |
| JP | 2011512961 A | 4/2011 | |
| JP | 2011-516865 A | 5/2011 | |
| JP | 2011-519689 A | 7/2011 | |
| JP | 2012510885 A | 5/2012 | |
| JP | 2012-521852 A | 9/2012 | |
| JP | 2012520127 A | 9/2012 | |
| JP | 2012210381 A | 11/2012 | |
| JP | 2013541389 A | 11/2013 | |
| JP | 2016073723 A | 5/2016 | |
| WO | 2006006958 A | 1/2006 | |
| WO | 2008057573 A2 | 5/2008 | |
| WO | 2008086613 A1 | 7/2008 | |
| WO | 2008086615 A1 | 7/2008 | |
| WO | 2008086616 A1 | 7/2008 | |
| WO | 2009009802 A1 | 1/2009 | |
| WO | 2009137659 A1 | 11/2009 | |
| WO | 2010029935 A1 | 3/2010 | |
| WO | 2010/104775 A2 | 9/2010 | |
| WO | 2010137375 A1 | 12/2010 | |
| WO | 2011/039955 A1 | 4/2011 | |
| WO | 2012/061940 A1 | 5/2012 | |
| WO | 2012091903 A1 | 7/2012 | |
| WO | 2013033592 A1 | 3/2013 | |
| WO | 2014077871 A2 | 5/2014 | |

OTHER PUBLICATIONS

Ketterling et al. 2006 IEEE Trans. Ultrason. Ferroelec. Freq. Cont. 53:1376-1380 (Year: 2006).*

Li et al 2010 Applied Phys. Lett. 97: article 133702 4 pages (Year: 2010).*

English translation of Japanese Office Action for Japanese Patent Application No. 2017-246030 dated Oct. 23, 2018 (7 pages).

Yin et al., "Novel combined miniature optical coherence tomography ultrasound probe for in vivo intravascular imaging", J. Biomed Optics, Jun. 2011 vol. 16(6), 4 pages.

Bezerra et al., "Intracoronary Optical Coherence Tomography: A Comprehensive Review", JACC: Cardiovascular interventions, (2009) 2:11, pp. 1035-1046.

Herickhoff et al., "Dual-mode IVUS Transducer for Image-Guided Brain Therapy: Preliminary Experiments", Ultrasound Med Biol. Oct. 2011; 37(10): 1667-1676.

Mao et al. "Fiber lenses for ultra-small probes used in optical coherent tomography", J. Biomedical Science and Engineering, Mar. 2010, 27-34.

(56) References Cited

OTHER PUBLICATIONS

Prati et al., "Intracoronary optical coherence tomography, basic theory and image acquisition techniques", Int. J. Cardiovasc. Imaging (2011) 27: 251-258.
Tsai et al., "Piezoelectric-transducer-based miniature catheter for ultrahigh-speed endoscopic optical coherence tomography", Biomedical Optics Express, 2:8, Aug. 1, 2011, pp. 2438-2448.
Extended European Search Report for Application No. PCT/US2013/024628 dated Jun. 16, 2016 (7 pages).
International Search Report and the Written Opinion of the International Searching Authority for International Application No. PCT/US2013/024620 dated Apr. 5, 2013 (14 pgs.).
Li et al., "Hybrid Intravascular Ultrasound and Optical Coherence Tomography Catheter for Imaging of Coronary Atherosclerosis", Catherization and Cardiovascular Interventions 81:494-507 (2013).
Bourantas et al., "Hybrid Intravascular Imaging—Current Applications and Prospective Potential in the Study of Coronary Athersclerosis", JACC 61:13 1369-1378 (2013).
Prati et al., "Expert review document part 2: methodology, terminology and clinical applications of optical coherence tomography for the assessment of interventional procedures", European Heart Journal, May 31, 2012 (pp. 1-10).
Yang et aL, "A Dual-Modality Probe Utilizing Intravascular Ultrasound and Optical Coherence Tomography for Intravascular Imaging Applications", IEEE Transactions of Ultrasonics, Ferroelectrics, and Frequency Control 57:12 2839-2843 (2010).
Translation of Office Action mailed from Japanese Patent Office dated Oct. 22, 2013 for Japanese Patent Application No. 2009-536291 (4 pages).
Translation of Office Action mailed from Japanese Patent Office dated Oct. 22, 2013 for Japanese Patent Application No. 2013-131070 (4 pages).
International Search Report and the Written Opinion of the International Searching Authority for International Application No. PCT/US2007/023493 dated Apr. 23, 2008 (17 pages).
Search Report for Japanese Patent Application No. 2015-543025 dated Nov. 14, 2016. 12 pgs.
Office Action for Japanese Patent Application No. 2015-543025 dated Dec. 13, 2016. 5 pgs.
Search Report for Japanese Patent Application No. 2019-210995 dated Aug. 11, 2020. 9 pgs.
Extended Search Report for Application No. PCT/US2013024620, mailed from European Patent Office on Jun. 21, 2016 (12 pages).
JP 2018-108342, Notice of Reason(s) for Rejection, dated Mar. 19, 2019.
Extended European Search Report for Application No. 23218841.7 dated Apr. 9, 2024 (6 pages).
Search Report for Japanese Patent Application No. 2015-543026 dated Nov. 16, 2016. 15 pgs.
Office Action for Japanese Patent Application No. 2015-543026 dated Nov. 29, 2016. 3 pgs.
Search Report for Japanese Patent Application No. 2017-246030 dated Aug. 21, 2018. 8 pgs.
Search Report for Japanese Patent Application No. 2019-186748 dated Jul. 16, 2020. 9 pgs.

\* cited by examiner

MULTIMODAL IMAGING SYSTEMS PROBES AND METHODS

CROSS-REFERENCE TO RELATED APPLICATIONS

This application is a continuation of U.S. patent application Ser. No. 13/758,528, filed on Feb. 4, 2013, which claims priority to and the benefit of U.S. Patent Provisional Patent Application No. 61/727,997, filed on Nov. 19, 2012, and U.S. Provisional Patent Application 61/728,006, filed on Nov. 19, 2012, the entire disclosures of each of which are herein incorporated by reference.

FIELD OF INVENTION

This invention relates to the field of imaging and more specifically to data collection probes and components thereof suitable for use with optical coherence tomography and other imaging technologies, such as ultrasound.

BACKGROUND

Coronary artery disease is one of the leading causes of death worldwide. The ability to better diagnose, monitor, and treat coronary artery diseases can be of life saving importance. Optical coherence tomography (OCT) is a catheter-based imaging modality that uses light to penetrate a sample such as blood vessel walls and generate images of the same. These images are valuable for the study of the vascular wall architecture and blood vessel geometry. Intravascular ultrasound (IVUS) is another imaging technology that can be used to image a blood vessel. The images generated using OCT are of a higher resolution and more clearly depict structures such as plaques and stent struts as well as other objects and characteristics of interest when imaging a blood vessel.

Conversely, IVUS has a better penetration depth relative to OCT. IVUS can typically penetrate tissue, such as a vessel wall, within the range of about 4 mm to about 8 mm. Unfortunately, IVUS images are typically of a lower resolution, which can make interpreting them more challenging. OCT has a shorter penetration depth and can typically penetrate tissue, such as a vessel wall, within the range of about 2 mm to about 3 mm. Given the respective advantages of OCT and IVUS in terms of imaging depth and otherwise, a need exists to develop systems that integrate these two imaging modalities such that their respective advantages may be combined without their associated disadvantages.

The present invention addresses these needs and others.

SUMMARY OF INVENTION

In one aspect, the invention relates to an image data collection system such as a probe that includes an optical data collection subsystem and an ultrasound data collection subsystem. The optical data collection subsystem can be configured to collect data for optical coherence tomography. The ultrasound data collection subsystem, or a portion thereof, generates incident acoustic waves while the optical data collection subsystem, or a portion thereof, directs incident light waves. In turn, each of these two subsystems receives returning acoustic waves and returning light waves, respectively, from a sample. Each received wave can be compared relative to the incident waves or other data to evaluate the sample, for example, by generating ultrasound and OCT images of the sample. Specifically, the received waves can be analyzed as signals that are each associated with the two imaging modalities, one being light based and the other being acoustic wave based. In one embodiment, the optical data collection subsystem and the ultrasound image data collection subsystem both emit their light and acoustic waves, respectively, substantially perpendicular to or at a predetermined angle relative to the longitudinal axis of a probe or another axis offset therefrom. Typically, the probe is rotatable within and translatable along a blood vessel. In one embodiment, the probe can be component in an image data collection system.

In one embodiment, the ultrasound subsystem is positioned distal relative to the optical subsystem and both subsystems are offset from each other by a predetermined distance. Both subsystems generate beams of acoustic and light waves, respectively, that can be substantially parallel or at an angle relative to each other. In one embodiment, the offset of the two beams causes each beam to collect data relative to the same region of a tissue sample at different points in time. Further, for embodiments in which the ultrasound subsystem rotates along with the OCT subsystem, the delay between where each respective subsystem is collecting data relative to the sample can be measured in terms of the pullback speed relative to the offset distance between each respective data collection subsystem. In one embodiment, the data collection subsystems are disposed coaxially relative to each other and include a beam director and an acoustic transducer, respectively.

In one embodiment, the relative position and respective speed of rotation for the OCT beam and the ultrasound beam are configured to maintain the quality of either the resultant IVUS image or the OCT image or both images. Further, the probe can also be configured such that the IVUS and OCT image data can be used to reconstruct a combined image along the same scan line.

In one embodiment, the ultrasound data collection subsystem is an ultrasound transducer and the optical data collection subsystem is a beam director. In turn, each of the optical beam director and the ultrasound transducer can be components of a probe tip. In one embodiment, the probe tip can be disposed in a sheath suitable for introducing into a blood vessel and imaging through the sheath. The sheath can include a transparent window configured to align with the beam director and ultrasound transducer such that a vessel wall can be imaged. In one embodiment, the sheath or portions thereof of optically and acoustically transparent such that light and acoustic waves can pass there through and image data can be obtained with respect to a sample. In one embodiment, the sheath includes an optically and acoustically transparent window.

In one embodiment, optically and acoustically transparent means that sufficient light and acoustic waves are transmitted through the window such that an OCT image and an ultrasound image can be generated. The sheath can cause acoustic beam reflections, optical beam reflections, or both. In one embodiment, an optical beam director and an acoustic beam generator are positioned such the optical beam and the acoustic beam are angled relative to each other such that direct reflections from such a sheath are prevented or reduced. Accordingly, in part the invention relates to angling and/or positioning the optical beam director and acoustic beam generator to increase the signal to noise ratio in the resultant OCT, IVUS or combination images. In part, this can be achieved by reducing the noise contribution of sheath-scattered optical or acoustic beams when collecting optical and acoustic signals for a given sample.

In one aspect, the invention relates to an image data collection system. The system includes a data collection probe. The data collection probe includes a sheath and a probe tip. The probe tip includes an optical data collection subsystem and an acoustic data collection subsystem positioned distally relative to the optical data collection subsystem; and a probe body, the probe tip and the probe body disposed in the sheath, the probe body comprising an optical fiber in optical communication with the optical data collection subsystem.

In one aspect, the invention relates to a dual modality image data collection system. The dual modes are ultrasound and optical coherence tomography in one embodiment. The system can include a data collection probe, a patient interface unit (PIU) and an image processor. In one embodiment, the PIU includes a PIU connector port. In one embodiment, the image processor includes an OCT system and an IVUS system such that each respective system is configured to receive data collected using a probe that includes a probe tip described herein. In one embodiment, the image processor includes one or more data acquisitions systems (DAS) such as a data acquisition card, a processor, and an interferometer. In one embodiment, the probe includes a sheath and a probe tip. The probe tip includes an optical beam director and an acoustic beam generator. In one embodiment, the beam director is configured to direct an optical beam having a center axis which can also be referred to as an optical center axis. In one embodiment, the ultrasonic transducer is configured to direct an acoustic beam or wave having a center axis which can also be referred to as an acoustic center axis. An optical fiber is disposed in the probe and in optical communication with the optical beam director. The optical fiber can define a longitudinal axis along which the optical beam director and acoustic beam generator are disposed. In one embodiment, the optical beam director and the acoustic beam director are positioned such that they generate an optical beam and an acoustic beam having a distance between the two beams that ranges between about 300 microns to 400 microns.

In one embodiment, the optical beam director and the acoustic beam director are positioned such that they generate an optical beam and an acoustic beam having a distance between the two beams that ranges between about 250 microns to 500 microns. In one embodiment, the distance between the two beams is measured from the center line or axis of each beam. In one embodiment, the optical beam has a width that ranges from about 20 microns to about 60 microns. In one embodiment, the acoustic beam has a width that ranges from about 200 microns to about 300 microns.

In one embodiment, the probe is configured to rotate by a motor in the PIU at a rate of from about 100 Hz to about 200 Hz. The PIU is configured to pull the probe at a speed of between about 18 mm/sec to about 36 mm/sec in one embodiment. In one embodiment, a rotatable connector or coupler and/or the probe are rotationally balanced to reduce noise and vibration during data collection at the rotation speeds and pullback speeds described herein. The connector port allows disposable probes that include sheaths and probe tips to be attached to the PIU and rotated thereby.

In one embodiment, the image processor is configured to generate scan lines at a rate of between about 25,000 lines/second to about 50,000 lines/second. In one embodiment, the image processor is configured to perform sample acquisition at a rate that ranges from about 6 MHz to about 12 MHz. In one embodiment, the electrical conductors are selected from the group of high conductance and high fatigue strength materials. In one embodiment, the helical pitch is between about 0.5 cm and about 1.5 cm.

The data collection probe can include an optical fiber, a probe tip in optical communication with the optical fiber, and a first conductor and a second conductor. The first and second conductors are helically wrapped around the optical fiber. In turn, the wrapped optical fiber is disposed within a torque cable also referred to as a torque wire. In one embodiment, the conductors wrapped around the optical fiber are oxygen free copper. In one embodiment, the outer jacket is disposed around the optical fiber. In turn, in one embodiment, the conductor is wrapped around the outer jacket. In one embodiment, the diameter of optical fiber including the outer jacket ranges from between about 100 to about 175 microns. The probe is configured to be rotationally balanced in one embodiment.

In one aspect, the invention relates to a method of collecting image data in a blood vessel. The method includes controlling a rate of rotation of a rotatable coupler, also referred to herein as a connector in some embodiments, such that movement of the blood vessel is reduced during the acquisition of optical coherence image data and ultrasound image data; transmitting optical coherence image data along an optical fiber through the rotatable coupler; and transmitting ultrasound image data along one or more conductors or conductive paths through the rotatable coupler. In one embodiment, the rate of rotation is between about 100 Hz and about 200 Hz. The method can further include controlling a rate of pullback through the blood vessel such that movement of the blood vessel is reduced during the acquisition of optical coherence image data and ultrasound image data. The rate of pullback can be between about 18 mm/sec and about 36 mm/sec.

In one aspect, the invention relates to an image data collection system. The system includes a data collection probe which includes: a sheath; a probe tip which includes a backing material defining a channel; an optical data collection subsystem, wherein a portion of the optical data collection system is disposed in the channel; and an acoustic data collection subsystem disposed above a region of the backing material and positioned distally relative to the optical data collection subsystem; and a probe body, the probe tip and the probe body disposed in the sheath, the probe body includes an optical fiber in optical communication with the optical data collection subsystem.

In one embodiment, the image data collection system further includes a torque wire defining a bore; a plurality of conductors wrapped around the optical fiber in a pattern, the conductors in electrical communication with the acoustic data collection subsystem, the conductor wrapped optical fiber disposed in the bore. In one embodiment, the optical data collection subsystem includes a beam director and the acoustic data collection subsystem includes an ultrasound transducer. In one embodiment, the pattern is a helical pattern having a helical pitch that ranges from between about 0.5 cm and about 1.5 cm. In one embodiment, the image data collection system further includes a patient interface unit (PIU) and an image data collect system in electrical communication with the PIU, the PIU configured to electrically couple the data collection probe to the image data collect system.

In one embodiment, the image data collect system acquires data from the acoustic data collection subsystem and the optical data collection subsystem at an acquisition rate that ranges from about 6 MHz to about 12 MHz. In one embodiment, the PIU includes a motor configured to retract the probe tip at a pullback rate that ranges from about 18 mm/second to about 50 mm/second. In one embodiment, the probe tip includes a first section and a second section, the second section flares outward related to the first section at a boundary between the respective sections, a portion of the channel spans the first section. In one embodiment, the probe tip has an endface that includes a curved boundary. In one embodiment, the beam director and ultrasound transducer are separated by a distance.

In one embodiment, the PIU includes a motor configured to rotate the data collection probe at a rate of rotation that ranges from about 100 Hz to about 200 Hz. In one embodiment, the beam director is angled to direct a beam at an angle that ranges from about 0 degrees to about 20 degrees relative to a normal to the longitudinal axis of the optical fiber. In one embodiment, the optical subsystem and the acoustic subsystem are positioned such that beams generated by each respective subsystem are substantially parallel. In one embodiment, the probe tip further includes a first elongate conductor and a second elongate conductor and wherein the beam director is positioned between the first elongate conductor and the second elongate conductor, each elongate conductor in electrical communication with the ultrasound transducer.

In one embodiment, the probe tip further includes a backing material, the transducer disposed on the backing material, the transducer having an acoustic wave directing surface disposed at an angle that ranges from about 5 degrees to about 15 degrees. In one embodiment, the acoustic subsystem and the optical subsystem are positioned coaxially to one another. In one embodiment, a resistance of the plurality of conductors ranges from about 5 ohms to about 20 ohms.

In one aspect, the invention relates to an image data collection system. The system includes a data collection probe comprising: a sheath; a probe tip comprising a backing material; an optical data collection subsystem comprising a beam director configured to direct a light beam having an optical center axis; and an acoustic data collection subsystem disposed above a region of the backing material and positioned distally relative to the optical data collection subsystem, the acoustic data collection system comprising an ultrasonic transducer configured to generate an acoustic wave having an acoustic center axis; and a probe body, the probe tip and the probe body disposed in the sheath, the probe body comprising an optical fiber in optical communication with the optical data collection subsystem, wherein the beam director and the ultrasonic transducer are positioned such that during probe rotational speeds ranging from about 100 Hz to about 200 Hz and data collection probe pullback speeds ranging from about 18 mm/sec to about 36 mm/sec, a time period between when the optical center axis and the acoustic center axis light beam cross a common reference point ranges from about M to about N.

In one embodiment, M is 0.01 seconds and N is 0.02 seconds. In one embodiment, M is about 1.2% of a cardiac cycle and seconds and N is about 2.4% of the cardiac cycle. In one embodiment, the backing material defines a channel and wherein a portion of the optical data collection system is disposed in the channel. In one embodiment, the image data collection system further includes a torque wire defining a bore; a plurality of conductors wrapped around the optical fiber in a pattern, the conductors in electrical communication with the acoustic data collection subsystem, the conductor wrapped optical fiber disposed in the bore. In one embodiment, wherein the pattern is a helical pattern having a helical pitch that ranges from between about 0.5 cm and about 1.5 cm.

In one embodiment, the image data collection system further includes a patient interface unit (PIU) and an image data collect system in electrical communication with the PIU, the PIU configured to electrically couple the data collection probe to the image data collect system. In one embodiment, the image data collect system acquires data from the acoustic data collection subsystem and the optical data collection subsystem at an acquisition rate that ranges from about 6 MHz to about 12 MHz. In one embodiment, the PIU includes a motor configured to retract the probe tip at a pullback rate that ranges from about 18 mm/second to about 50 mm/second. In one embodiment, the probe tip includes a first section and a second section, the second section flares outward related to the first section at a boundary between the respective sections, a portion of the channel spans the first section. In one embodiment, the probe tip has an endface that includes a curved boundary. In one embodiment, the beam director and ultrasound transducer are separated by a distance In one embodiment, the PIU includes a motor configured to rotate the data collection probe at a rate of rotation that ranges from about 100 Hz to about 200 Hz. In one embodiment, the beam director is angled to direct a beam at an angle that ranges from about 0 degrees to about 20 degrees relative to a normal to the longitudinal axis of the optical fiber. In one embodiment, the optical subsystem and the acoustic subsystem are positioned such that beams generated by each respective subsystem are substantially parallel.

In one embodiment, the probe tip further includes a first elongate conductor and a second elongate conductor and wherein the beam director is positioned between the first elongate conductor and the second elongate conductor, each elongate conductor in electrical communication with the ultrasound transducer. In one embodiment, the transducer is disposed on the backing material, the transducer having an acoustic wave directing surface disposed at an angle that ranges from about 5 degrees to about 15 degrees. In one embodiment, the acoustic subsystem and the optical subsystem are positioned coaxially to one another. In one embodiment, a resistance of the plurality of conductors ranges from about 5 ohms to about 20 ohms.

In one aspect, the invention relates to image data collection system. The system includes a data collection probe comprising: a sheath; a probe tip comprising a backing material defining a channel; an optical data collection subsystem, wherein a portion of the optical data collection system is disposed in the channel; and an acoustic data collection subsystem disposed above a region of the backing material and positioned distally relative to the optical data collection subsystem; and a probe body, the probe tip and the probe body disposed in the sheath, the probe body comprising an optical fiber in optical communication with the optical data collection subsystem.

In one embodiment, the optical data collection subsystem includes a beam director and the acoustic data collection subsystem includes an ultrasound transducer. In one embodiment, the transducer is disposed on the backing material, the transducer having an acoustic wave directing surface disposed at an angle that ranges from about 5 degrees to about 15 degrees. In one embodiment, The image data collection system further includes a torque wire defining a bore; a plurality of conductors wrapped around the optical fiber in a pattern, the conductors in electrical communication with the acoustic data collection subsystem, the conductor wrapped optical fiber disposed in the bore. In one embodiment, the pattern is a helical pattern having a helical pitch that ranges from between about 0.5 cm and about 1.5 cm. In one embodiment, the beam director is angled to direct a beam at an angle that ranges from about 0 degrees to about 20 degrees relative to a normal to the longitudinal axis of the optical fiber.

In one aspect, the invention relates to a method of collecting image data in a blood vessel having a wall. The method includes rotating a probe tip includes an optical beam director and an ultrasound transducer at a rate of rotation; transmitting incident optical and acoustic waves using the optical beam director and ultrasound transducer, respectively; receiving optical and acoustic waves reflected from the wall using the optical beam director and ultrasound transducer, respectively; pulling the probe tip back through the blood vessel at a pullback rate, acquiring an OCT data set and an ultrasound data set in response to the received optical and acoustic waves reflected from the wall; and controlling the rate of rotation such that movement of the blood vessel is reduced during the acquisition of the reflected optical and acoustic waves from the wall.

In one embodiment, the method further includes the step of generating one or more images of sections of the wall using the OCT data set, the ultrasound data set, or both the OCT data set and the ultrasound data set. In one embodiment, the method further includes the step of controlling the pullback rate such that the pullback rate ranges from about 18 mm/second to about 50 mm/second. In one embodiment, the rate of rotation is controlled such that the rate of rotation ranges from about 100 Hz to about 200 Hz. In one embodiment, the OCT data set and the ultrasound data set are acquired at a sample acquisition rate that ranges from about 6 MHz to about 12 MHz. In one embodiment, the OCT data set and the ultrasound data set are acquired at a line acquisition rate that ranges from 25 kHz to about 50 kHz. In one embodiment, the method further includes the step of controlling the rate of rotation and the pullback rate such that a time period between when an optical center axis and an acoustic center axis cross a common reference point ranges from about M to about N. In one embodiment, M is 0.01 seconds and N is 0.02 seconds. In one embodiment, M is about 1.2% of a cardiac cycle and N is 2.4% of the cardiac cycle.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

In part, the invention relates to a multimodal data collection probe that collects data suitable for imaging a vessel or lumen of interest and related methods, systems, subsystems and other components. The probe is multimodal because two or more data collection modes can be used. These modes can operate simultaneously or sequentially. The modes can be any suitable imaging technology such as optical coherence tomography, ultrasound, or others as well as be specified based on the type of waves used such as acoustic or light waves. The probe can include devices or systems that are configured to collect data for each respective imaging modality such as beam directors and acoustic wave generators.

In one embodiment, the probe is configured for use in a lumen of a body such as an artery or other blood vessel. For example, the probe can be configured to collect optical coherence tomography (OCT) data and ultrasound (IVUS) data using light waves and acoustic waves, respectively. The data collected using one or more of the probe embodiments described herein can be used to generate an image of vessel, determine a fractional flow reserve, measure pressure in a lumen or collect data relating to other parameters or structures of interest.

One or more probe embodiments can include a first receiver and a second receiver. Each of these receivers is configured to receive a signal such as an acoustic or optical signal. The first and second receivers can be, for example, receivers, transceivers, transducers, detectors, apparatus or subsystems. In one embodiment, the first receiver is an intravascular ultrasound apparatus or subsystem and the second receiver in an optical coherence tomography apparatus or subsystem. The receivers are also configured to generate or direct signals such as acoustic waves and light waves. For example, the first receiver can include an ultrasound device that generates and receives acoustic waves. Similarly, as an example, the second receiver can include an optical device that transmits light to a sample and receives light from the sample. In one embodiment, the first receiver is distal to the second receiver. In other embodiments, the first receiver can be adjacent to, in contact with, abutting or otherwise positioned relative to the second receiver in various configurations.

The respective optical or acoustic beams or beam originating surfaces can be substantially parallel or skewed relative to each other. In one embodiment, an optical receiver is positioned such that it is adjacent to and proximal to an ultrasound receiver. A backing material can be used to surround a portion of the optical beam generating element and form a surface suitable for supporting the ultrasound element. A housing or cover can be used to partially surround the backing material. Additional details relating to exemplary system and probe embodiments are described herein.

Figure 1:
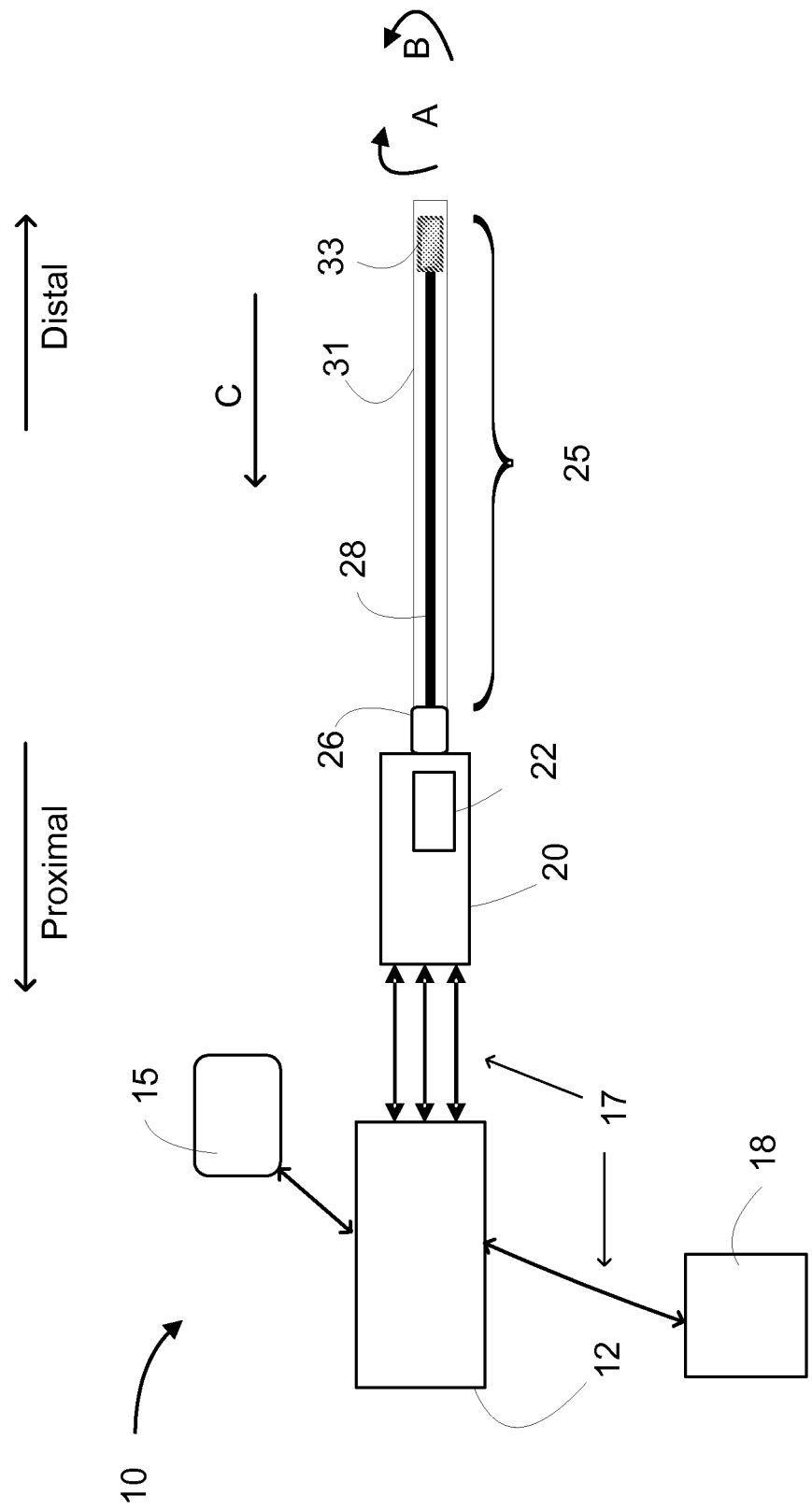
FIG. 1 is a schematic diagram of an image data collection system in accordance with an illustrative embodiment of the invention.

FIG. 1 illustrates a multi-modal system 10 suitable for use with various probes and imaging modalities. The multi-modal system 10 includes an image data acquisition system 12. The data acquisition system 12 is configured to collect multi-channel data in one embodiment such as OCT data and ultrasound data. The image data acquisition system can include a data acquisition device that is in electrical communication with a processor. The data acquisition system 12 can be configured to process multiple channels such as channels containing OCT image data and IVUS image data. In addition, the multi-modal system 10 can include one or more displays 15 suitable for displaying an image of a sample generated using image data such as an OCT, IVUS, or combination OCT and IVUS image of a blood vessel. In one embodiment, the data acquisition system 12 converts the raw image data collected using the probe into images that can be viewed by a user on display 15 or other displays. The display 15 can also be used to display a graphical user interface to manipulate the image data or control the image data acquisition session.

One or more signal lines 17 and/or one or more control lines 17 are in electrical (whether by wire or wirelessly), in optical, or otherwise in communication with the image data acquisition system 12. In one embodiment, one line or bus is used to transmit control signals and image data. One or more components 18 can be in electrical or optical communication with data acquisition system 12. In one embodiment, such one or more components 18 can include an interferometer having a sample arm and a reference arm, optical fibers, an optical receiver, one or more clock generators, an ultrasound pulser, ultrasound receiver, and other components of OCT and IVUS systems.

In one embodiment, the multi-modal system 10 includes a patient interface unit (PIU) 20. In one embodiment, the PIU 20 connects two imaging components or subsystems such as ultrasound and OCT components of the probe 25 with the image data acquisition system 12 through one of the control lines or signal lines 17. The control or signal lines 17 are bi-directional such that data can flow in one or both directions along a given line. Typically, control signals are transmitted from the system 12 to the PIU 20 and signals are transmitted from the PIU 20 to the probe tip 33 through an optical path and an electrically conductive path that is formed when the probe 25 is coupled to connector 26. In one embodiment, the PIU 20 and the probe 25 include sections of optical fiber that constitute sections of the sample arm of an interferometer. The PIU also includes conductors such as lengths of wire used to transmit ultrasound data and control signals. Signal lines 17 can include optical paths such as optical fibers that are part of the sample arm and conductors or circuit elements that transmit ultrasound data and control signals.

The PIU 20 includes a rotatable connector 26 configured to connect to an image data collection probe 25 and release from such a probe 25. In one embodiment, the probes 25 are designed to be disposed of after a given data collection procedure. Accordingly, the connector 26 allows probes that have been used to image a vessel to be removed and new probes to be optically and electrically coupled to the PIU 20. The probe 25 is configured to rotate in response to being driven by a motor. One or more motors can be disposed in the PIU 20 in one embodiment such one or more motors are shown by exemplary motor 22. While rotating in a blood vessel, the probe 25 can collect image data with respect to a surface of a blood vessel as it is pulled back through the vessel and relay that data along electrical and optical paths that span the PIU 20 and signal lines 17 to connect to the system 12. In one embodiment, the PIU 20 includes one or more electrical couplers and one or more optical couplers to connect electrical and optical components or subsystems of the probe to electrical and optical components or subsystems of the system 12. One or more of such couplers can be disposed in or a component of the connector 26.

In one embodiment, the smallest data unit in an OCT or IVUS image is called a sample. Further, a sequence of samples along a ray originating from a probe 25 to the maximum imaging depth is called a scan line. The ray typically originates from a component of the probe tip 33 such as an optical beam director or an acoustic beam generator. The probe includes a probe body 28. The probe body 28 includes one or more sections of optical fiber that are arranged to form an optical path and rotate in response to the action of a motor. A beam director having a light receiving and transmitting surface is in optical communication with one or more optical fiber sections disposed in the probe body. The one or more rotatable optical fibers that are part of the probe body 28 are disposed in sheath 31. The sheath 31 is an outer body or section of a catheter in one embodiment. The sheath can include a transparent window through which optical and acoustic image data can be collected.

Figure 3A:
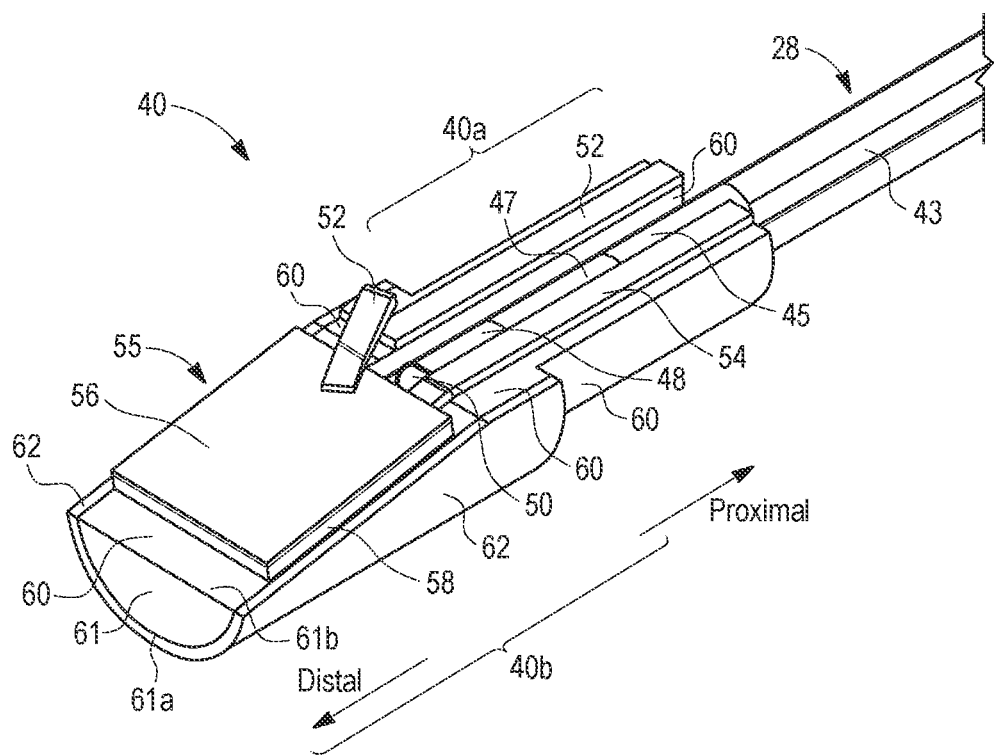
FIG. 3A is a schematic diagram showing a perspective view of a portion of an image data collection probe in accordance with an illustrative embodiment of the invention.

The beam director is located within the sheath 31 in one embodiment and is part of a data collection subsystem 33. The data collection subsystem 33 can also be referred to as a probe tip or cap 33. The probe tip 33 includes an optical beam director and an acoustic beam director in one embodiment. Additional details relating to an exemplary probe tip 33 are shown in FIG. 3A which depicts probe tip 40 as an embodiment of the general probe tip 33 of FIG. 1. As shown, probe tip 40 includes ultrasound and optical data collection subsystems.

One or more conductors in electrical communication with the acoustic beam generator of a probe tip such as probe tip 33 can be wrapped around one or more lengths of optical fiber in the probe body 28. These wrapped conductors in the probe body 28 which surround an optical fiber can be disposed in a torque wire as described herein. Additionally, such wrapped conductors can be in electrical communication with a rotary transformer or other conducting element disposed in connector 26 or PIU 20 when the probe 25 is coupled to the PIU 20. In one embodiment, these various systems and components are suitable for collecting data that can be used to generate an image of a sample by scanning the sample as the probe body, probe tip, and sheath rotate.

Figure 6A:
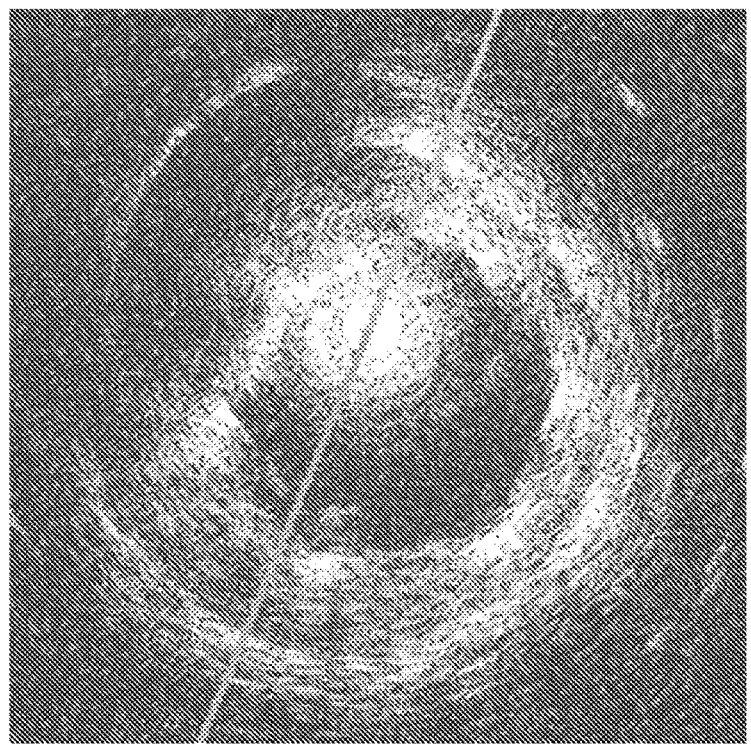
FIG. 6A is an IVUS image showing penetration depth and resolution in accordance with an illustrative embodiment of the invention.
Figure 6B:
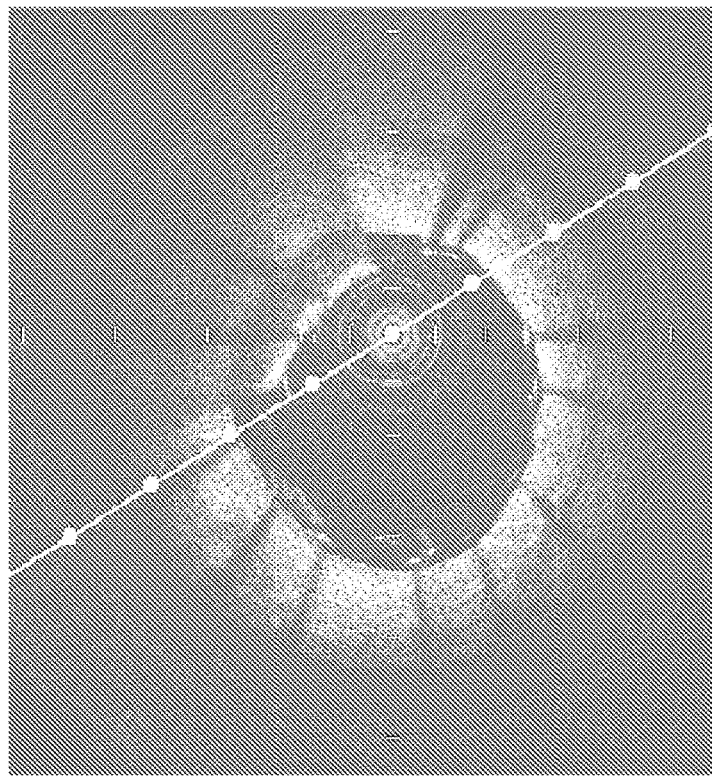
FIG. 6B is an OCT image showing penetration depth and resolution in accordance with an illustrative embodiment of the invention.

The OCT and IVUS images are typically acquired one scan line at a time. A cross-sectional image is then formed from a set of scan lines collected as the probe 25 rotates. Examples of some exemplary images are shown in FIGS. 6A-6B. Further, to image a segment of an artery or other blood vessel, the probe, alternatively referred to as a catheter, is moved longitudinally while rotating such as during a withdrawal or pullback through a blood vessel. The probe can rotate in either a clockwise A or counterclockwise B direction. The probe is pulled back in a direction C away from the patient being imaged as it rotates in direction A or B. In this way, the probe acquires a set of cross-sectional images in a spiral pattern. The images originate from the various scan lines associated with a slice of the vessel or artery of interest. The image can be displayed as cross-sections along one or more axes on display 15. In one embodiment, the data acquisition system 12 converts the raw image data collected using the probe into images that can be viewed by a user on display 15 or other displays.

Figure 2A:
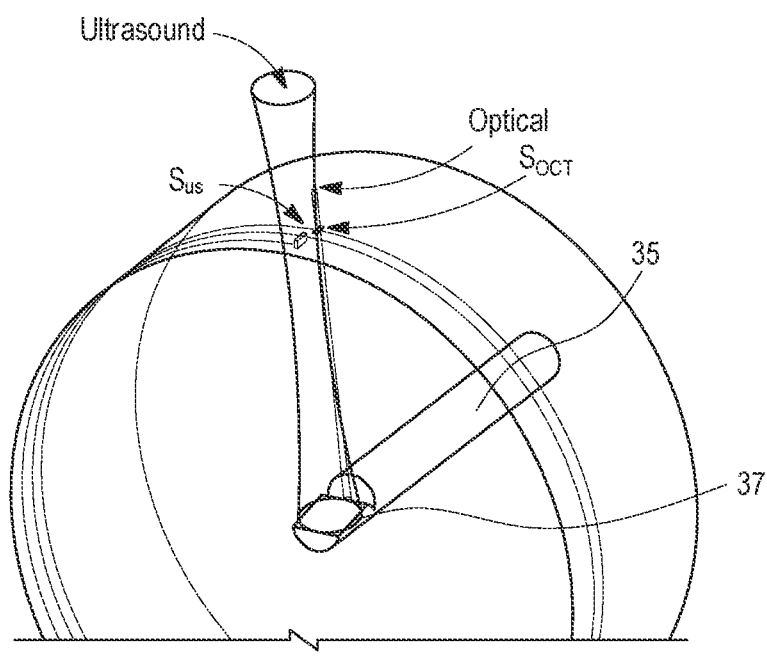
FIGS. 2A-2C are schematic diagrams depicting perspective views of rotating ultrasound and optical beams originating from an image data collection probe in accordance with an illustrative embodiment of the invention.
Figure 2B:
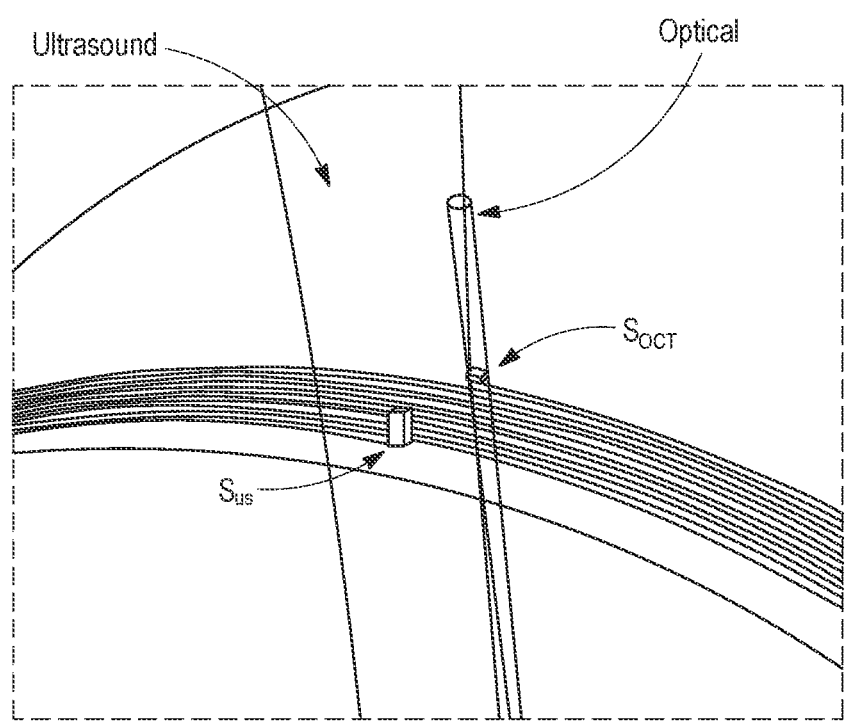
Figure 2C:
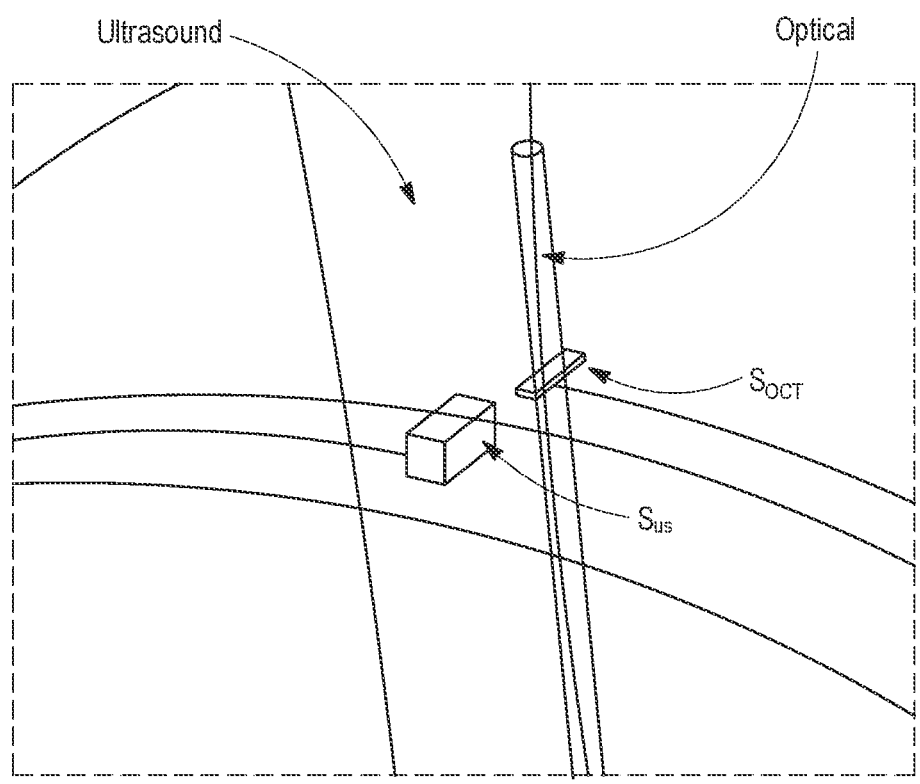

FIGS. 2A-2C show schematic representations of the intravascular image acquisition for a dual modality probe 35 configured such that the probe's two imaging beams are axially displaced. As shown, in FIG. 2A a probe tip 33 of a probe 35 has an ultrasound component disposed distally relative to an optical component. The two parallel beams (labeled ultrasound and optical) represent a pulse of energy each sent along its respective single scan line. The helical path in each of FIGS. 2A-2C shows how many probe 35 rotations are required (at a specific rotation rate and pullback speed) for the ultrasound or acoustic beam to illuminate the space previously illuminated by the axially displaced optical beam.

Each of FIGS. 2A-2C also shows two rectangular blocks $S_{OCT}$ and $S_{US}$. These blocks represent the sample size of the IVUS and OCT images. The height of the sample box (axial sample size) is determined by how many samples are taken in an imaging line and the maximum depth of penetration. The width of the box (rotational sample size) is determined by how many scan lines are taken in a single rotation and how from the sensor the specific sample is from the rotational center of the probe. The depth of the box (transverse sample size) is determined by how fast the pullback occurs relative to the rotation rate of the probe tip 33. In one embodiment, the probe 35 is rotated such that rapid dual mode acquisition is achieved by which IVUS and OCT data can be collected without the blood vessel undergoing a degree of motion that would introduce imaging artifacts or unacceptable noise into the IVUS or OCT images.

Table 1 below summarizes the imaging parameters used in rapid dual mode acquisition according to an embodiment of the invention and conventional IVUS scanning FIGS. 2A and 2C show the path traced by two embodiments of the invention that are configured for rapid acquisition of ultrasound and OCT data. FIG. 2B shows the path traced by an embodiment of the invention at conventional rates of rotation and pullback for an ultrasound probe configured for IVUS imaging. From Table 1 and Table 2 it is clear based on the of Rapid Acquisition values to Conventional IVUS values, that the Rapid Acquisition values represent significant increases of the applicable rates and speeds relative to conventional IVUS systems.

TABLE 1

| Description | Samples per line | Lines per Frame | Rotation Rate [Hz] | Pullback Speed [mm/sec] |
| --- | --- | --- | --- | --- |
| Rapid acquisition probe embodiment | about 250 | about 250 | about 100 to about 200 | about 18 to about 36 |
| Conventional IVUS | 250 | 250 | 15 to 30 | 0.5 to 1 |
| Ratio of Rapid Acquisition to Conventional IVUS values | about 1 | about 1 | about 6.67 | about 36 |

For a given dual mode data collection probe, the optical and acoustic beams can either be coincident or separated by some distance. While for image acquisition and alignment it would be optimum to have the beams coincident, constructing coincident beams require the two beam receivers/beam generators to overlap and leads to inevitable degradations in the performance of the data collection probe. Axially displacing the two data collection subsystems from each other (with the IVUS beam generator distal to the OCT beam director) allows the sensors to be built without compromise but does result in the two beams being spaced apart. In one embodiment, minimizing the axial displacement is an important design feature of a dual mode data collection probe As a result, positioning the IVUS transducer and the OCT beam director coaxially with an axial displacement between them that ranges from about 300 to about 500 microns is about as small as is practical without impacting the performance of one or both of the IVUS and optical data collecting components. Table 2 below highlights the differences and benefits associated with acquiring image data at conventional IVUS acquisition speeds and rapid acquisition speeds.

TABLE 2

| Description | Transverse Sample Size [microns] | Line Acquisition Rate [kHz] | Sample Acquisition Rate [MHz] | Theoretical IVUS penetration depth [mm] | Fraction of heart rate occurring between OCT and IVUS scan |
| --- | --- | --- | --- | --- | --- |
| Rapid acquisition embodiment | about 180 | about 25 to about 50 | about 6.25 to about 12.5 | about 15 to about 30 | about .024 to about .012 |
| Conventional IVUS | 33 | 3.75 to 7.5 | 1 to 2 | 100 to 200 | .86 to .43 |
| Ratio of Rapid Acquisition to Conventional IVUS values | about 5.45 | about 6.67 | about 6.25 | about .15 | about .0279 |

In Table 2, the transverse sample size is obtained as the ratio of the pullback speed to the rotation rate. The scan line acquisition rate is the scan lines per frame multiplied by the rotation rate. The sample acquisition rate is the samples per scan line multiplied by the scan line acquisition rate. Theoretical IVUS penetration depth is the theoretical depth an ultrasound wave can travel in water (at 1540 m/sec) and reflect back during a single sample acquisition time period. In turn, the fraction of heart rate occurring between the OCT and IVUS scan is based upon a 72 bpm heart rate and how long it takes the ultrasound data collection element to travel 0.360 mm at the pullback speed.

In addition, Table 2 provides support for the considerations and compromises available when re-aligning images obtained with two axially displaced data collection elements such as a beam director and an ultrasound transceiver as part of a co-registration process or other image data processing method. In one embodiment, the pullback speed is controlled to essentially freeze the motion of the lumen (vessel) so the two imaging modalities can be substantially overlaid or co-registered. For example, this can be achieved by having a pullback speed or rate that ranges from about 18 to about 36 mm/sec. In one embodiment the pullback speed or rate ranges from 18 to about 50 mm/sec. This allows image data collection to be performed when the lumen is not moving such a cross-sectional "snap shot" can be obtained by the rotating probe and associated acoustic and optical data collection subsystems disposed in the probe.

Performing a pullback at the rates described herein stretches the transverse sample size while reducing resolution along the lumen (vessel). In addition, performing a pullback at the rates described herein decreases the IVUS penetration depth by reducing the time available to wait for the returning ultrasound echoes. In contrast, imaging at pullback speeds and rotation rates near conventional IVUS values (as shown in Table 2) result in unacceptable motion blur between the IVUS and OCT images. This occurs, in part, because of lumen movement based on blood moving therethrough as the heart beats. In turn, imaging a vessel using pullback speeds and rotation rates above the rapid acquisition values, such as greater than about 36 mm/second, is problematic. Specifically, such excessive pullback speeds result in unacceptable IVUS imaging depth restrictions. Imaging at pullback speeds and rotation rates near the pullback rates described herein results in a reduction in motion blur and an increase IVUS penetration depth. As a result, an improved signal to noise ratio for images generated using such pullback rates with the data collection probe embodiments.

To achieve these imaging results with a probe having an axially displaced optical beam director and acoustic beam generator, various operating parameters and attributes are first established and then controlled within certain predetermined thresholds such as the values provided above in Tables 1 and 2 and otherwise recited herein. Specifically, in one embodiment line transmit rates are selected or set such that are between about 25 kHz to about 50 kHz. In turn, in one embodiment sample acquisition rates are selected or set such that are between about 6 MHz to about 12 MHz. The pullback during which image data is collected is set to occur within a predetermined time period at a pullback rate that ranges from about 18 mm/sec to about 36 mm/sec. Similarly, during the pullback, the probe having the optical and acoustic beam propagating components is rotated at a rate of probe rotation that ranges from about 100 Hz to about 200 Hz. In addition, the distances between the optical beam and the acoustic beam are configured such that the distance between the two respective beams ranges from about 300 to about 500 microns.

In one embodiment, when collecting data for imaging a vessel at the rapid acquisition speeds, the system processor is configured to generate ultrasonic pulses at a rate that ranges from about 25 kHz to about 50 kHz. Similarly, the data acquisition system is configured to acquire samples at a rate that ranges from about 6 MHz to about 12 MHz.

Probe Tip Embodiments

FIG. 3A shows an exemplary probe tip or cap 40 suitable for collecting image data with respect to a sample such an artery or other blood vessel. This probe tip can be rotated and pulled back as a component of a probe using the rapid acquisition values and rates described herein. The probe tip 40 is disposed within a sheath (not shown) and is attached to a probe body in one embodiment. For example, as shown in FIG. 1 a probe tip 33 is disposed in sheath 31 and connected to probe body 28. In FIG. 3A, the optical fiber section 43 is part of the probe body.

The probe tip 40 can include a first probe tip section 40a and a second section probe tip 40b. The junction of the first and second probe tip sections can denote a transitional boundary in which the width of the probe tip 40 changes as the second section 40b has a an outer surface which flares out or is wider relative to the outer surface of the first section 40a. In one embodiment, the probe tip 40 is configured to use a first imaging mode such as ultrasound and a second imaging mode such as optical coherence tomography. Accordingly, an optical beam and an acoustic beam propagate from the probe tip 40. Similarly, an optical beam and an acoustic beam are scattered or reflected from the sample, such as a blood vessel wall and then received by the optical and acoustic subsystems. These received waves are sent as optical and electrical signals along respective optical and conductive paths in the probe body through the PIU until they are received by the data acquisition system.

Specifically, the optical beam is directed from the probe tip 40 after the beam's constituent light is generated from an optical source and transmitted along one or more optical fibers or other optical paths which are sections of the sample arm of an interferometer. For example, with respect to FIG. 1, the optical source and interferometer can each be a component 18 of system 10. Similarly, as shown in FIG. 3A, the optical fiber 43 is a section of the sample arm of the interferometer. The optical fiber 43 has a jacket applied to it along some sections thereof. In FIG. 3A, no jacket is present on optical fiber 43 near the sections wherein the optical fiber 43 is fused to another fiber section such as beam expander 45.

The section of the probe body 28 shown includes an optical fiber 43. In one embodiment, conductive elements such as one or more wires connect to the electrical conductors 52, 54 which serve as two contacts or electrodes for the acoustic wave generator. The conductive elements continue from conductors 52, 54 and wrap around the optical fiber 43 in a pattern as described herein and continue as part of the probe body 28. These wrapped conductive elements can be disposed within a torque cable (not shown). As a result, the torque cable can be part of the probe body with the optical fiber 43 and the conductive elements disposed in the torque cable. These electrical conductive elements are shown relative to the optical fiber section and a torque wire in FIGS. 4A and 4B.

The optical fiber 43 is in optical communication with a beam director 50 such as a lens, lens assembly or other beam directing system. The beam director 50 can include the angled end face of an optical fiber section. The optical fiber 43 terminates at the beam director 50 in one embodiment. As shown, in an exemplary embodiment in FIG. 3A the optical fiber 43 is in optical communication with one or more optical fiber portions. These optical fiber portions or sections can include without limitation a grin lens or other portions of an optical train such as a beam expander 45, a GRIN lens 47, and a coreless optical fiber section 48. These optical elements are described in more detail herein.

As shown in this embodiment, the optical fiber 43 is in optical communication with a first coreless beam expander 45 which expands the beam transmitted along optical fiber 43 from the optical source. The beam expander 45 is in turn in optical communication with a GRIN lens optical fiber portion 47 which collimates the beam. Another coreless optical fiber section 48 is in optical communication with the GRIN lens 47. In one embodiment, the coreless optical fiber section 48 includes a beam director 50 at its terminus or endface. The beam director 50 in one embodiment includes an angled reflective surface that is metalized and formed at the end of the fiber portion 48. The beam director 50 can be configured to direct light at an angle C as shown.

Figure 3B:
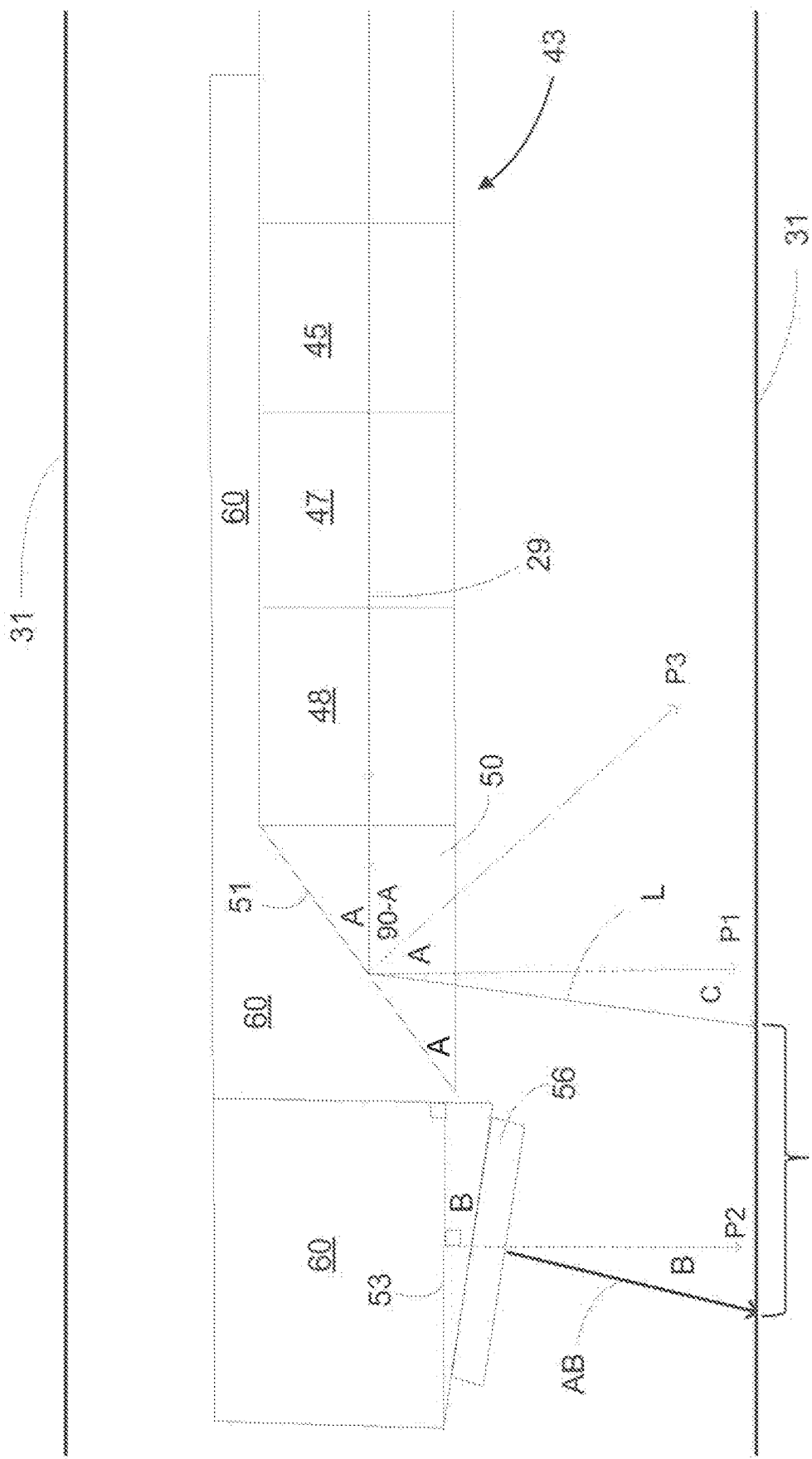
FIG. 3B is a schematic diagram showing a cross-sectional view of a portion of an image data collection probe and optical and acoustic angular orientations in accordance with an illustrative embodiment of the invention.

As shown in the cross-sectional view of FIG. 3B, the beam director 50 can be angled at an angle A relative to the longitudinal axis 29 of the optical fiber 43. Three perpendicular vectors or rays P1, P2, P3 are shown to provide a reference frame in FIG. 3B. P1 is normal to the axis 29. P2 is normal to the axis 29 and/or a ray 53 passing through the backing material 60 as shown. In one embodiment, light propagates along a fiber core that is substantially aligned with axis 29 from a source. After the light is reflected from the beam director 50, it is then directed through sheath 31 to a sample as light L. An acoustic wave AB is also directed to the sample. The angle A of the reflective surface 51 of the beam director 50 is about 40 degrees relative to the longitudinal axis 29 or a ray parallel thereto in one embodiment. In one embodiment, the angle C is approximately equal to (90 degrees-2A degrees). In one embodiment, A ranges from about 30 degrees to about 50. In one embodiment, A ranges from about 35 degrees to about 45. The acoustic beam AB and the light beam L can be separated by a distance BD which can be measured relative to the centers of each of these two beams. In one embodiment, BD ranges from about 250 microns to about 500 microns.

In one embodiment, the angle of the reflective surface of the beam director 50 is selected such that it is greater than or less than 45 degrees. When the angle is about 40 degrees, a first light ray propagating from the beam director will strike a portion of the sheath (not shown) such as the transparent window at an 80 degree angle measured relative to the longitudinal axis of the optical fiber. Since the angle of incidence at the sheath surface is less than about 90 degrees back reflections from the sheath are reduced. Therefore, in one embodiment, the angle of the light beam impinging on the sheath from the beam director is configured to be less than about 90 degrees and greater than about 70 degrees. The beam director 50 in one embodiment is concentric with axis of catheter rotation. Light travelling along optical fiber 43 is directed by the side projecting lens structure (45, 47, 48, and 50) such that the projected light beam impinges on a vessel wall when the probe tip 40 is disposed in a lumen.

Although the OCT system is optically-based, the ultrasound system uses electrical control signals to drive a transducer to produce acoustic waves. These waves can be shaped to form a beam. The data collected using the transducer also needs to be transmitted from the probe tip 40 along the probe body 28 for image formation. As discussed above, two electrical conductors or electrodes 52, 54 are disposed on either side of the beam director 50 as shown. The first and second electrical conductors 52, 54 serve as electrical signal lines for the ultrasound detector or transducer 55. The transducer 55 is an example of an acoustic data collection subsystem or a component thereof. In one embodiment, the transducer 55 includes a stack of layers that include a piezoelectric material such as Lead zirconate titanate (PZT).

In one embodiment, the transducer 55 has an uppermost acoustic matching layer 56 of the ultrasound generating stack (additional matching layers are possible). The first conductor 52 is in electrical communication with the ultrasound transducer 55 such as through layer 56 as shown. Acoustic beams are directed at an angle from the surface of layer 56 in one embodiment of the invention. The second conductor 54 is in electrical communication with the bottom or lower metalized surface of the piezoelectric material layer 58. Thus, in one embodiment, conductors 52 and 54 are in electrical communication with acoustic wave generating transducer 55 through one or more layers of the transducer 55.

The ultrasound transducer 55 and the beam director 50 can each be oriented at angles B and C as shown in FIG. 3B. In one embodiment, angles B and C are selected to be substantially the same. Angle B and angle C can range from 0 degrees to about 20 degrees. Angles B and C can be measured relative to a perpendicular to the longitudinal axis of the optical fiber portions such as optical fiber 43. In one embodiment, B is about 10 degrees. In one embodiment, C is about 10 degrees. In one embodiment, the beams generated from transducer 55 and director 50 are parallel or substantially parallel. In one embodiment, the advantage of tilting both the acoustic beam and the optical beam is to avoid direct reflections from the sheath in which probe tip 40 is disposed (not shown) such as sheath 31 in FIG. 1. In one embodiment, the ultrasound transducer 55 includes a piezoelectric stack. The length of the piezoelectric stack in one embodiment ranges from about 400 microns to about 800 microns. The height of the piezoelectric stack in one embodiment ranges from about 40 microns to about 80 microns. The thickness or width of the piezoelectric stack in one embodiment ranges from about 300 microns to about 600 microns.

In one embodiment, an ultrasound absorbing backing material 60 is disposed behind the transducer 55. This backing material 60 also provides support for the beam director 50 and transducer 55. A cover or housing 62 may be attached to and/or partially surrounds the backing material 60. In one embodiment, the cover or housing 62 is optional. The backing material can include particles of a dense material disposed in another material such as an epoxy. In one embodiment, tungsten particles can be disposed in an epoxy as the backing material. Ceramic materials and other dense particles can be used as the backing material. This cover or housing 62 in one embodiment includes radio-opaque material to increase visibility of the probe tip when an angiographic image is obtained of a patient during a pullback. In addition, the cover or housing 62 can include a higher strength metal to improve structural integrity of the probe tip and the optical and acoustic data collection elements.

In one embodiment, the backing material 60 can be shaped to form a support for the beam director. For example, in one embodiment the backing material 60 defines a channel or trench for the optical fiber to be disposed in as shown. In one embodiment, the probe tip has an endface 61 that has a curved cross-sectional portion or boundary such as, for example, a cross-section that includes a section of a circle, ellipse, or other curve. In one embodiment, the probe tip has a tapered geometry such that the cross-sectional area along it length changes from the endface to the end of a fiber receiving section. In one embodiment, the endface 61 includes a curved boundary 61a, such as the lower curve shown, and a substantially linear boundary 61b.

The trench or channel, which spans section 40a in one embodiment, is configured and sized to receive an optical fiber and/or other materials. Alternatively, the backing material 60 can define a planar support upon which the beam director 50 and transducer 55 are disposed. The cross-section of the probe tip 40 changes along the length in one embodiment. For example, a portion of the section of the probe tip 40 that includes the trench or channel defined by the backing material has a first width that is less than the width of the probe tip where the backing material supports the transducer 55. As shown in FIG. 3B, backing material 60 can be machined and/or molded to form a region that supports the beam director 50 and one or more fiber-based elements in optical communication with optical fiber 43 and a region that supports transducer 56. In one embodiment, the cross-section of the backing material surrounding a portion of the beam director 48 has a width that is greater than the width of the cross-section of the backing material surrounding a portion of optical fiber 43 (if disposed in the channel or groove), the beam expander 45, or the GRIN lens 47.

As shown in FIG. 3A, the probe tip 40 has an ultrasound transducer 55 at its distal end with the optical beam director 50 as close to the ultrasound transducer 55 as possible. In this configuration, during data collection, the centers of the optical and ultrasound beams are separated by at least ½ the dimension of the transducer and beam director combined. For a typical transducer 55 as described above, this application of transducer and beam director dimensions specifies, in one embodiment, a minimum separation distance between the beam director (optical data collection subsystem) and the ultrasound transducer (acoustic data collection subsystem) that ranges from about 300 to about 400 microns.

The relative placement of the ultrasound beam generator and the optical beam director overcomes several problems associated with other design options. Specifically, by positioning an ultrasound data collecting element in front of, above or alternatively distal to the optical data collecting element neither imaging modality is compromised to an unacceptable level.

To understand some of the other advantages of the placement of the ultrasound data collection component and the OCT data collection component in FIG. 3A, it is informative to consider alterative placement options relating to such components or portions thereof. For example, as one alternative embodiment to the arrangement of FIG. 3A, the optical beam director is placed in front of (distal to) the ultrasound beam generator. This embodiment requires the optical fiber transmitting the OCT image data to pass through the ultrasound backing material. In turn, this compromises the ultrasound backing material (thereby both introducing spurious reflections and reducing the amount of backing to absorb reflected energy) and shifts one of the optical or acoustic data collecting elements off the axis of rotation (either reducing ultrasound sensor area or increasing OCT path length).

As a second embodiment, placing the optical and ultrasound beams coincident requires shifting one or both data collection elements off the axis of rotation (reducing ultrasound transducer size), as well as compromising the ultrasound data collection subsystem's performance (by either shadowing it or requiring holes and tunnels through the ultrasound transducer for the optical fiber and optical beam). In addition, as a third embodiment, the optical and ultrasound beams can be diametrically opposed. Such an option requires shifting both data collection elements off the axis of rotation (reducing ultrasound size), compromising the ultrasound backing material, and subjecting the beam reconstruction to non-uniform rotational distortion effects.

As discussed above with respect to FIG. 3A, the probe tip 40 is part of a data collection probe configured to collect optical data and acoustic data such that OCT and IVUS images can be generated. The probe tip is connected to a probe body 28 in one embodiment. The probe body includes optical and electrical paths by which signals are sent to and received from the probe tip. Additional details relating to probe body embodiments are shown in FIGS. 4A and 4B and as discussed above with respect to FIG. 1.

Figure 4A:
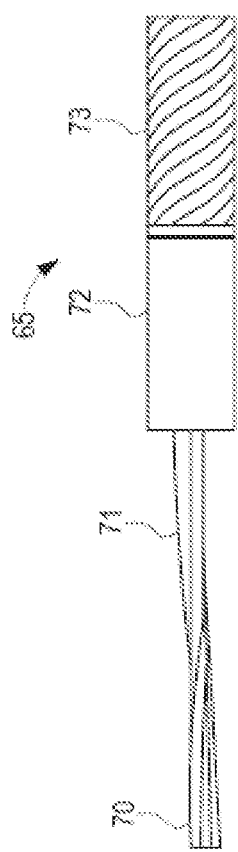
FIG. 4A is an image of a portion of a probe body in accordance with an illustrative embodiment of the invention.
Figure 4B:
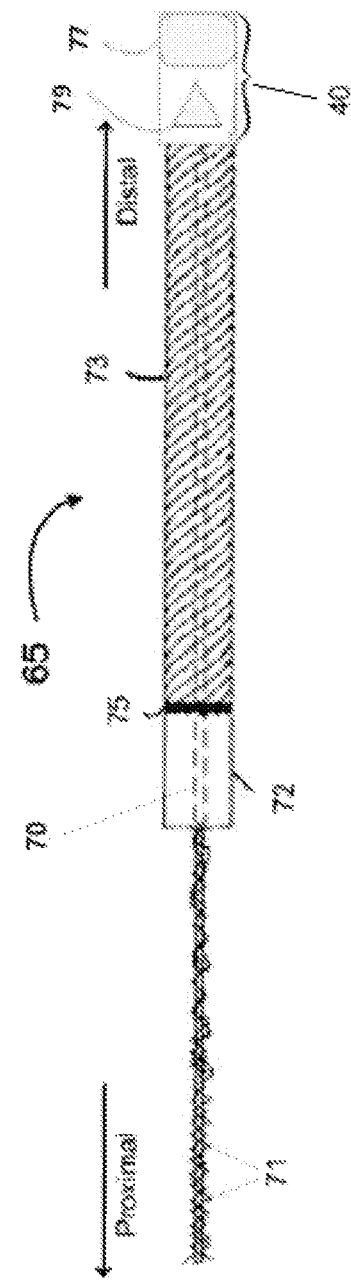
FIG. 4B is a schematic diagram of a probe body and a probe tip in accordance with an illustrative embodiment of the invention.

In more detail, FIGS. 4A and 4B depicts a section of a probe body 65. As shown in FIG. 4A, the probe body includes the coated optical fiber 70 (preferentially ranging from about 125 microns to about 155 microns in diameter). The fiber 70 is centrally disposed of relative to other components of the probe body. Wrapped around the optical fiber 70 are a number of individual electrical conductors 71. These conductors 71 can be wires or other rigid or flexible conductors. These electrical conductors 71 are symmetrically wrapped around the optical fiber to maintain rotational balance or rotational equilibrium when the optical fiber rotates during data collection and otherwise. A radiopaque component 72 such as a marker can be used in one embodiment. This radiopaque marker 72 can be a metal sleeve or another device that will show up on x-rays such as used for angiography.

A torque wire 73 receives a section of the fiber 70 and the conductors 71. The marker 72 can be welded or otherwise joined to the torque wire 73 as shown by joint 76 in FIG. 4B. In FIG. 4B, the proximal and distal directions corresponding to those shown in FIGS. 1 and 3 are shown. On the right side of FIG. 4B, the optical fiber 70 is shown with dotted lines to indicating that it is disposed within the torque wire 73. The electrical conductors 71 continue to be wrapped around the fiber 70 within the torque wire. The conductors 71 are shown continuing past the marker 72 in FIG. 4B. In one embodiment, the end of the fiber 70 and conductors terminate at terminal or probe connector. A probe tip 75 is shown attached to the probe body 65. In turn, the probe tip includes an acoustic data collection subsystem 77 such as a transducer that is disposed relative to an optical data collection subsystem 79 such as a beam director as components of the probe tip 75. The optical element 79 is positioned proximally to the acoustic element 77 as shown.

The electrical conductors 71 are circuit components which constitute sections of the electrical conductive path between the acoustic data collection element 77 which extend along the probe body and the PIU until the path reaches the data collection system. Given their role in transmitting control signals and ultrasound data, in one embodiment, conductors 71 are selected to have a low real resistance. In addition, the conductors are selected such that the impedance of the conductors and any circuit elements or devices that constitute the ultrasound signal transmission electronics are matched to the impedance of the ultrasound signal receiver electronics of system 12. In one embodiment, the diameter of the wrapped fiber and the pitch of the helical pattern are used adjust the impedance of the transmitter electronics such that it matches the impedance of the receiver electronics. For example, in one embodiment the resistance of conductors 71 is less than about 20 ohms in one embodiment. In another embodiment, the resistance is less than about 10 ohms. In one embodiment, the impedance of the conductors used ranges from about 50 to about 100 ohms.

In one embodiment, the helically wound assembly of conductors 71 over the optical fiber 70 is configured as a twisted pair transmission line. In one embodiment, uniform spacing of the helical twist symmetrically rotates the position of a first conductor relative to a second conductor and allows for a rejection (or cancelling) of introduced noise from external fields. Tighter helical pitches remove more noise, looser helical pitches allow more cable flexibility. For example, in one embodiment the pitch is chosen to be from between about 0.5 mm to about 1.5 mm to balance noise reduction relative to cable flexibility.

The wound assembly of conductors 71 and optical fiber 70 is configured to be fatigue resistance. In one embodiment the plurality of conductors 71 can involve two pairs of conductors. Two pairs of 44 gauge oxygen free copper conductors (high conductance and high fatigue strength) wrapped with a helical pitch of about 0.5 to about 1.0 cm satisfy the resistance and impedance ranges described herein. As a result of wrapping the electrical conductors 71 around the optical fiber 70, the overall diameter of the wrapped fiber increases such that it ranges from about 0.009" to about 0.011". This assembly of optical fiber 70 and wrapped conductors 71 is partially disposed inside of the torque cable 73. The conductors 71 are in electrical communication with conductors disposed in probe tip 65 and acoustic element 79. In one embodiment, attached at the end of the torque cable 73 is a radiograph opaque marker 72. This marker improves visibility of the probe tip 65 and provides a solid material to connect the probe tip 65.

The torque cable 73 is a helical series of wires wound in two opposing directions so the cable has rotational stiffness (transmits torque) but is flexible in bending. The torque cable 73 is similar to those used in IVUS alone or OCT alone catheters. The difficulty in the combined catheter is fitting both the electrical and optical elements inside the torque cable 73 without compromising their performance characteristics. Increasing the outer diameter of the torque cable is not desirable because the sheath and guide catheter also then need to be increased. As a result, the probe would need something larger than the typical 5 or 6 French guide catheter used in catheterization lab procedures.

Figure 5A:
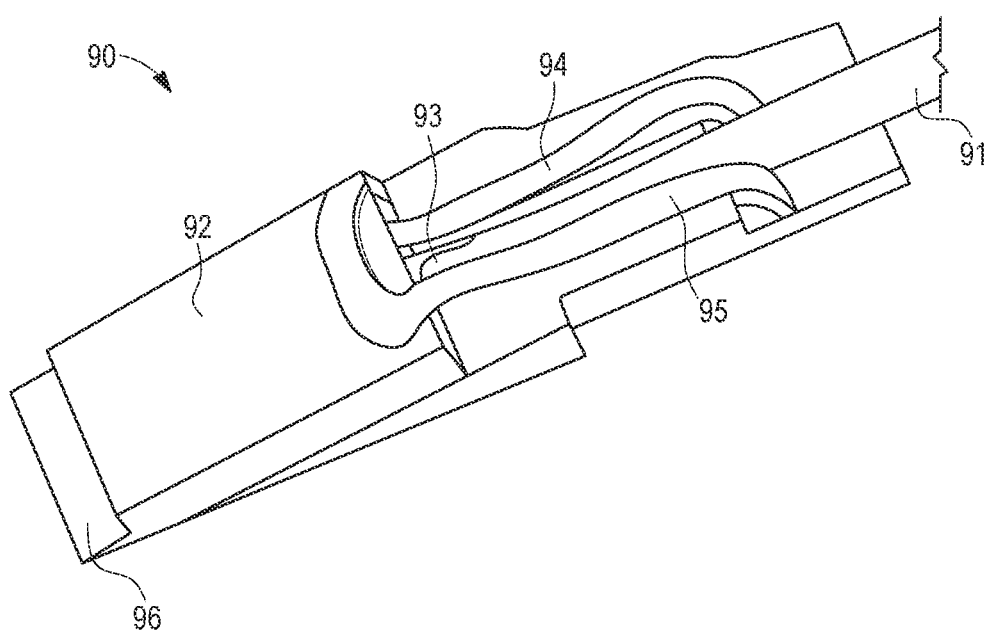
FIGS. 5A-5C are images depicting different components of multi-modal data collection probes in accordance with an illustrative embodiment of the invention.

FIG. 5A shows a probe tip 90 that includes an ultrasound transducer 92 also referred to as an acoustic or ultrasound data collection subsystem or component thereof. An optical fiber 91 that is part of the probe body is shown disposed relative to components of the probe tip 90. The beam director 93 which is configured to send and receive imaging light is also part of the probe tip 90. In addition, as shown conductors 94, 95 are in electrical communication with the ultrasound transducer 92 such as by being bonded to contact points on the probe tip 90. The conductors 94, 95 are disposed on either side of the beam director 93. The conductors 94 are used to transmit signals to control the ultrasound transducer 92. Conductors 94, 95 can serve as contact points for conductive elements such as wires which are configured to wrap around fiber 91. The ultrasound transducer 92 is disposed on a backing material 96 in one embodiment as shown. The backing material 92 can have an arrow head shape with flared sides and a narrowed neck portion near the optical fiber. The backing material can also be shaped to be a section of a cone or other conic section such as frustum in one embodiment.

Figure 5B:
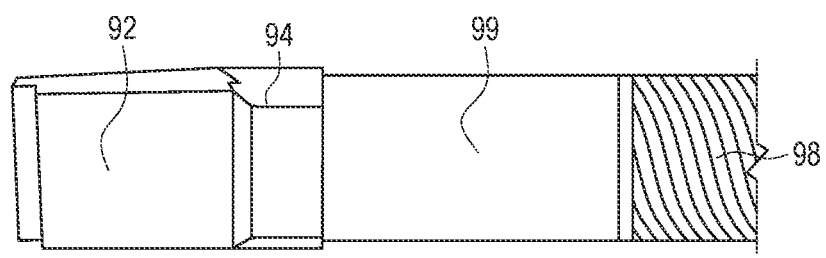

FIG. 5B shows a probe tip 90. The torque cable or wire 98 has an optical fiber at least partially disposed therein that is in optical communication with beam director 93. In one embodiment, the torque cable or wire 98 can include a radio-opaque marker 99 positioned near the probe tip 90. The probe tip 90 is attached to the marker 99 in one embodiment. In turn, the marker 99 can be attached to torque wire 98.

Figure 5C:
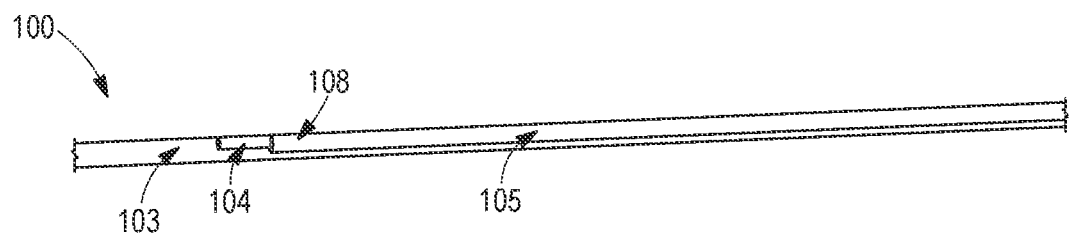

FIG. 5C shows a section of a data collection probe 100. The sheath 103 is shown with the probe tip 104 disposed therein. This probe tip 104 includes a beam director and an ultrasound transducer. The torque cable 105 is disposed inside the sheath 100. A radiopaque marker 108 is adjacent to and attached to the probe tip 104 and the torque cable 105.

The probe tips and related features described herein can be used to generated cross-sectional views of blood vessels such as arteries. An example of such cross-sectional views can be seen in FIGS. 6A and 6B. FIG. 6A is an IVUS image showing penetration depth and resolution generated using a processor-based system and a data set collected using a data collection probe having an ultrasound transducer as described herein. The IVUS image of FIG. 6A shows the penetration depth (relative to OCT) that IVUS is able to achieve. FIG. 6B is an OCT image showing penetration depth and resolution generated using a processor-based system and a data set collected using a data collection probe having a beam director as described herein. The OCT image of FIG. 6B shows the enhanced resolution (relative to IVUS) that OCT is able to achieve.

In the description, the invention is discussed in the context of optical coherence tomography; however, these embodiments are not intended to be limiting and those skilled in the art will appreciate that the invention can also be used for other imaging and diagnostic modalities or optical systems in general.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

The invention claimed is:

1. An image data collection system comprising:
 a data collection probe to be inserted in a patient comprising:
  a sheath;
  a torque wire;
  a radiopaque marker comprising a first end and a second end, the first end attached to the torque wire;
  a probe tip comprising:
   a backing material support comprising:
   an ultrasound absorbing material;
   an elongate section defining a channel;
   an angled support section adjacent the elongate section;
   an optical data collection subsystem comprising an optical fiber and a beam director configured to direct a light beam having an optical center axis,
   an acoustic data collection subsystem comprising an ultrasonic transducer having a distal end and a proximal end, the ultrasonic transducer supported by the angled support section wherein the probe tip, the radiopaque marker, and the torque wire are disposed in the sheath;
 a patient interface unit including a motor arranged to retract the probe tip; and
 a controller that adjusts the pullback rate and the rate of rotation such that a time period between when the optical center axis and the acoustic center axis cross a common reference point is based on a cardiac cycle of the patient.

2. The image data collection system of claim 1 wherein the optical fiber is disposed below and between a first conductor and a second conductor, each conductor in electrical communication with the ultrasonic transducer, wherein sections of each of the first conductor and the second conductor are disposed within the radiopaque marker and torque wire.

3. The image data collection system of claim 1 wherein a distal end of the channel is defined by the ultrasound absorbing material forming the angled support section wherein the ultrasound absorbing material forms the elongate section.

4. The image data collection system of claim 1 wherein the probe tip is configured such that an angle of the light beam impinging on the sheath from the beam director is configured to be less than about 90 degrees and greater than about 70 degrees to reduce back reflections from the sheath.

5. The image data collection system of claim 1 further comprising an image data collection subsystem that acquires data from the ultrasound transducer and the optical data collection subsystem at an acquisition rate that ranges from 6 MHz to 12 MHz.

6. The image data collection system of claim 1 wherein the probe tip is attached to the radiopaque marker.

7. The image data collection system of claim 1 wherein the probe tip has an endface that includes a curved boundary.

8. The image data collection system of claim 1 wherein the beam director directs the light beam in a first direction and the ultrasound transducer directs the acoustic wave in the first direction, wherein the light beam and the acoustic wave are separated by a distance.

9. The image data collection system of claim 1 wherein the beam director is angled to direct a beam at an angle that ranges from 0 degrees to 20 degrees relative to a normal to the longitudinal axis of the optical fiber.

10. The image data collection system of claim 1 wherein the beam director and the ultrasound transducer are positioned such that beams generated by each of them are parallel.

11. The image data collection system of claim 1 wherein the probe tip further comprises a first elongate conductor and a second elongate conductor and wherein the beam director is positioned between the first elongate conductor and the second elongate conductor, each elongate conductor in electrical communication with the ultrasound transducer.

12. The image data collection system of claim 1 wherein the transducer has an acoustic wave directing surface disposed at an angle that ranges from 5 degrees to 15 degrees.

13. The image data collection system of claim 1 wherein the acoustic ultrasound transducer and the beam director are positioned coaxially to one another.

14. The image data collection system of claim 1 further comprising a torque wire defining a bore and a plurality of conductors wrapped around the optical fiber in a pattern, the conductors in electrical communication with the acoustic data collection subsystem, the conductor wrapped optical fiber disposed the bore.

15. The image data collection system of claim 14 wherein the pattern is a helical pattern having a helical pitch that ranges from between 0.5 mm to 1.5 mm.

16. The image data collection system of claim 14 wherein a resistance of the plurality of conductors ranges from 5 ohms to 20 ohms.

17. A method of collecting image data in a blood vessel of a patient having a wall comprising the steps of:
   rotating a probe tip comprising an optical beam director and an ultrasound transducer;
   transmitting incident optical and acoustic waves through a sheath using the optical beam director and ultrasound transducer, respectively;
   receiving optical and acoustic waves reflected from the wall using the optical beam director and ultrasound transducer, respectively;
   pulling the probe tip back through the blood vessel;
   sampling OCT data and ultrasound data in response to the received optical and acoustic waves reflected from the wall; and
   adjusting the rate of rotation and the pullback rate such that a time period between when the optical center axis and the acoustic center axis cross a common reference point is based on a cardiac cycle of the patient.

18. The method of claim 17 further comprising the step of generating one or more images of sections of the wall using the OCT data the ultrasound data, or both the OCT data and the ultrasound data.

19. The method of claim 17 wherein the OCT data and the ultrasound data are acquired at a line acquisition rate that ranges from 25 kHz to 50 kHz.

* * * * *